US006579263B1

United States Patent
Chernack

(12) United States Patent
(10) Patent No.: US 6,579,263 B1
(45) Date of Patent: Jun. 17, 2003

(54) METHOD AND APPARATUS FOR THE DELIVERY OF CONTRAST FLUID TO A PATIENT

(76) Inventor: Milton Chernack, 15 W. 55th St., New York, NY (US) 10019

( * ) Notice: Subject to any disclaimer, the term of this patent is extended or adjusted under 35 U.S.C. 154(b) by 0 days.

(21) Appl. No.: 10/043,470

(22) Filed: Jan. 11, 2002

(51) Int. Cl.[7] .............................................. A61M 37/00
(52) U.S. Cl. ........................ 604/131; 604/247; 604/514; 604/186; 604/249
(58) Field of Search ................................ 604/131, 323, 604/514, 186, 249, 247, 248

*Primary Examiner*—Brian L. Casler
*Assistant Examiner*—Kathryn L. Thompson
(74) *Attorney, Agent, or Firm*—Cohen, Pontani, Lieberman & Pavane

(57) ABSTRACT

A contrast fluid delivery method and system includes a multiple-reuse filling section for attachment by conduit to a contrast fluid supply container, and a delivery section that is removably attached to the filling section for delivering contrast fluid held in the filling section to a patient. The filling section includes a main body having a fluid chamber, a contrast fluid filling inlet with a gravity-operated valve, an opening for connecting an operable power syringe, and a contrast fluid outlet fed through a spring-loaded one-way check valve. The delivery section includes a first delivery conduit connected between the contrast fluid outlet of the main body and the fluid inlet of an inline aspirator syringe, and a second delivery conduit connected at one end to a fluid outlet of the aspirator syringe and at the other to a catheter for delivering the contrast fluid to a patient. The aspirator syringe includes a spring-loaded plunger that is operatively depressed and released to confirm and assure patency of the delivery line before sustained injection of the desired volume of contrast agent. The filling section is isolated from contamination by the downstream delivery section and may be used repeatedly for successive patients, whereas the delivery section is discarded and replaced after each patient use.

18 Claims, 4 Drawing Sheets

METHOD AND APPARATUS FOR THE DELIVERY OF CONTRAST FLUID TO A PATIENT

BACKGROUND OF THE INVENTION

1. Field of the Invention

The invention relates to a method and system for injecting a fluid into a patient from a bulk container, and in particular to a method and system for so injecting or infusing contrast fluid which does not require disposal of the entire system, including the fluid supply container, after each patient use.

2. Description of Related Art

In the field of medical imaging, many procedures require the use of a contrast agent that is intravenously delivered to the patient, generally through the use of an associated power injector that controls the delivery rate and volume and predeterminately limits the pressure at which the contrast fluid is delivered. The current norm is to employ a disposable syringe that is bulky and costly, and a filling procedure that is difficult and time consuming. The syringe is intended for only a single use and is accordingly disposed of after each patient use. Present protocols also require that any contrast fluid that remains in the bottle or container of contrast fluid, once the container has been opened for use and/or fluid has been loaded into a syringe, be discarded. Since the contrast fluid is typically delivered in bulk containers which may hold far more fluid than is used for most imaging procedures, this often requires the disposal of a volume of yet unused contrast fluid. This entire process is thus extremely wasteful and costly to the medical system as a whole.

SUMMARY OF THE INVENTION

It is an accordingly the desideratum of the invention to avoid, or at least significantly reduce, the drawbacks and difficulties that are present in the use of prior art methods and apparatus, as for example hereinabove described, for the delivery of contrast fluid to a patient in medical imaging procedures.

It is a particular object of the invention to provide such a method and system that enables a technician to readily load a syringe and prepare for delivery of a contrast fluid to a patient in a simplified yet highly intuitive manner.

It is another object of the invention to provide such a method and system having a first part, into which contrast fluid from a bulk container is loaded, that can be used repeatedly with multiple patients without jeopardizing sterility of the system or remaining supply of contrast fluid, and a second part that is intended for a single use with a single patient.

It is a further object of the invention to provide such a two part system in which the relative manufacturing cost of the second, single-use part is considerably less than the manufacturing cost of the first, multiple-use part, thereby maximizing efficient management of contrast fluid delivery costs for the health care provider.

It is still another object to provide such a method and system in which the single-use disposable part, which is replaced for each patient, is relatively simple to use and inexpensive to manufacture yet provides high reliability and operating integrity.

The present invention is based on and requires reliable maintenance of fluid flow, in at least that portion of the inventive apparatus into which contrast fluid is loaded from the fluid container or source, in a single direction toward the patient while preventing all potentially-contaminating reverse flow, so that contamination of the syringe and of the bulk contrast source can be prevented. Toward that end, a system constructed in accordance with the invention includes a first or filling section which attaches to the bulk contrast source (and to the power syringe), and a second or delivery section that is connected between and communicates contrast fluid from the filling section to the patient. In this manner any possibility of contamination between the delivery section and the filling section is prevented. It is generally contemplated that the filling section will be used for multiple patients during an entire day of imaging procedures or operations, whereas the delivery section will be discarded and replaced after each patient use.

The filling section includes a main body that can be attached to any existing power or manually-operated syringe or injector, and the body defines a fluid holding chamber having an inlet and an outlet for the contrast fluid. The inlet is connected to a conventional or otherwise suitable vented spike, which is routinely used to pierce a contrast fluid container to access its contents for transfer of the contained fluid to another device, as by or through a coiled length of sterile medical tubing. The inlet is provided or associated with a gravity-operated valve formed by a stainless steel ball which seats in a conically-profiled ring or lip that surrounds or bounds the inlet. The ball rolls disengagingly off or away from the valve seat to thereby open the inlet when the main body is vertically tilted or oriented, whereupon the technician can use or operate the syringe to draw contrast fluid from the container into the filling section fluid chamber, and to then purge (back through the inlet) any air which has collected at the top of the fluid chamber. A spring loaded one-way check valve in or at or proximate the outlet insures that the purged air is directed toward the contrast container rather than downstream, toward the patient, to the delivery section of the inventive apparatus. The main body is then rotated or reoriented so that the contrast fluid outlet is disposed lower than the opposite end of the main body to which the syringe is connected, thereby activating or closing the gravity-operated ball valve and sealing closed the fluid path between the fluid holding chamber of the filling section and the contrast container. This orientation of the filling section additionally insures that any air that may yet be present in the fluid chamber rises to and remains at that portion of the main body to which the syringe is attached—i.e. remote from the outlet through which the contrast fluid is transferred to the delivery section of the apparatus—to thereby prevent unintended and potentially fatal injection of air into the patient. The filling section is then ready to be connected to the delivery section for injection or infusion of the contrast agent into the patient.

The delivery section includes a first fluid conduit—such as coiled, flexible, sterile tubing—having a first end that is attached to the outlet of the main body via at least one one-way check valve, and a second end that is attached to the inlet of an inline aspiration syringe. The aspiration syringe has a fluid chamber which is filled via an inlet and an outlet which is attached to a catheter by a second or delivery conduit in the form of another length of flexible, sterile, typically coiled tubing. The entire delivery system receives contrast fluid for infusion into the patient by means of the power or manually-operated loading syringe that is connected to the main body of the filling section. The aspiration syringe itself includes a spring loaded plunger which is used to confirm patency of the fluid path by manually depressing the plunger against the urgency of the spring and then releasing it to return the plunger to its initial position; patency is indicated by a visually-observable flow of blood from the patient into the second conduit for a distance of several inches. The process of injection or infusion, under the power of the main loading syringe, may then proceed. The aspiration syringe is furthermore constructed to avoid the need for additional valves, as have heretofore been required, to separately close its inlet during the patency confirmation; the plunger itself blocks and thereby closes the inlet—and thus prevents backflow into the first conduit—as the plunger is advanced from its initial position to inject contrast fluid into the patient and then returned to that initial position to draw a mixture of contrast fluid and patient blood back into the aspiration syringe fluid chamber. The delivery section or set is moreover low in cost, as contrasted with the relatively more costly and complex filling section, and is intended to be discarded and replaced after each patient use of the inventive apparatus.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the drawings, wherein like reference numerals denote similar elements throughout the several views and Figures.

DETAILED DESCRIPTION OF THE CURRENTLY PREFERRED EMBODIMENTS

Figure 1:
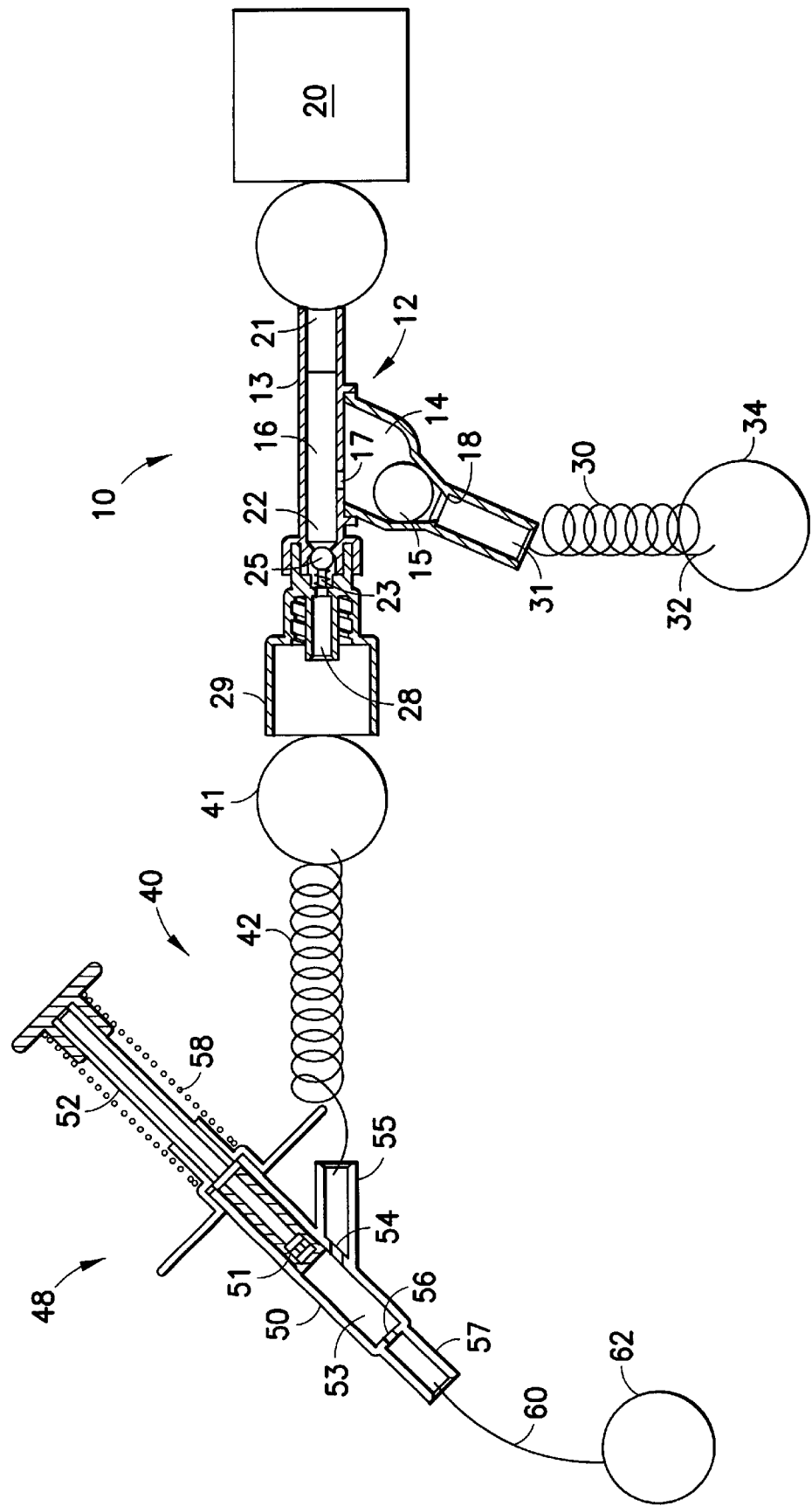
FIG. 1 is a schematic, side cross-sectional view of the contrast fluid delivery system of the present invention with the elements of the inventive system generally oriented and arranged for normal use in injecting contrast fluid into a patient.

FIG. 1 schematically depicts a system constructed in accordance with the present invention for delivering contrast fluid from a bulk fluid source to a patient. As there shown, the system includes a filling section 10 and a delivery section 40. With specific reference to FIGS. 2 and 3, the filling section 10 has a main body 12 that defines an interior fluid holding chamber 13 which is divided into a ball valve chamber 14 and a loading chamber 16 that are connected by a fluid passageway opening 17. The main body 12 is substantially T-shaped, although in the illustrated currently-preferred embodiment the base of the "T" meets the remainder of the body at an off-center location and, in addition, at a non-right angle. The ball chamber 14 captively contains a freely-movable ball 15, as for example a 0.375 inch steel ball, which in FIG. 3 is shown seated in the conical entrance to an inlet opening 18 that separates the ball chamber 14 from an inlet tube 19. The fluid passageway opening 17 is sized smaller than the diameter of ball 15 to maintain the ball captive within ball chamber 14. The ball 15 and inlet opening 18 together define a gravity-operated valve by which, when the body 12 is oriented in its FIG. 3 position so that gravity urges the ball into seated relation on or atop the preferably conical peripheral entrance or lip of inlet opening 18, the opening 18 is sealed against outward fluid flow therethrough so that contrast fluid contained or held within body 12 cannot flow outward through inlet tube 19. When, on the other hand, the main body 12 is oriented in its FIG. 2 position, gravity urges the ball 15 away from inlet opening 18 to thereby clear and open the inlet against bidirectional throughflow.

A loading and delivery syringe—as for example a conventional power syringe 20 (which, although generally contemplated and intended for use with the inventive contrast fluid delivery apparatus, forms no part of the inventive apparatus)—is connected (as by a conventional rotatable male luer on the body 12) to a first end 21 of the loading chamber 16 for operative use in initially drawing contrast fluid into the fluid holding chamber 13 through inlet tube 19 and valve opening 18, and for later delivering the contrast fluid from chamber 13 downstream to the patient for infusion at a predetermined rate and pressure. A chamber outlet 24 at the second or opposite end 22 of fluid loading chamber 16 is closed by a one-way pressure-operated check valve that is defined by a preferably conical lip or boundary wall of outlet 24 and a spring-loaded ball 25 which is urged under the force of a spring 23 onto the peripheral lip of outlet 24 to thereby normally close the check valve. The ball 25, which may for example be a 0.125 inch stainless steel ball, and its associated coil spring 23 are housed in a barrel 26 having an annular shoulder that seats the spring and forms a connection to a fluid delivery outlet tube 28 of filling section 10.

It should also be noted that although the device 20 which is operable for initial loading of the main body 12 with fluid and for subsequently delivering the loaded fluid downstream to the patient is herein described as a power syringe, any other apparatus or mechanisms for suitably accomplishing the same functionality in association with the main body of the filling section 10 may alternatively or additionally be employed as a general matter of availability and choice. The device 20, while intended and contemplated for use in association with the inventive delivery system, is as previously noted not a part of the inventive apparatus. Thus, the identity and selection of the particular loading and delivery device(s) 20 for attachment or connection to the first end 21 of body 12 in its generally intended and contemplated operating manner and environment is independent of the invention and its description herein as a power syringe is by way of illustrative example only.

A filling conduit 30, as for example in the form of a length of flexible, coiled, plastic sterile tubing, has a first end 31 which is connected in any suitable manner to the inlet tube 19 and a second end 32 that is provided with a conventional vented spike (not shown), as for example by releasable connection via a conventional male luer 34 attached to or carried by the second end 32, for piercing the top of a supply container (not shown) of contrast fluid so that its liquid contents can be selectively withdrawn from the container through filling conduit 30 and transferred into fluid holding chamber 13 when syringe 20 is conventionally operated for that purpose. The vented spike incorporates a microbial filter to allow air to enter the supply container to replace the contrast fluid so withdrawn from the container without contaminating the remaining fluid supply in the container.

Figure 2:
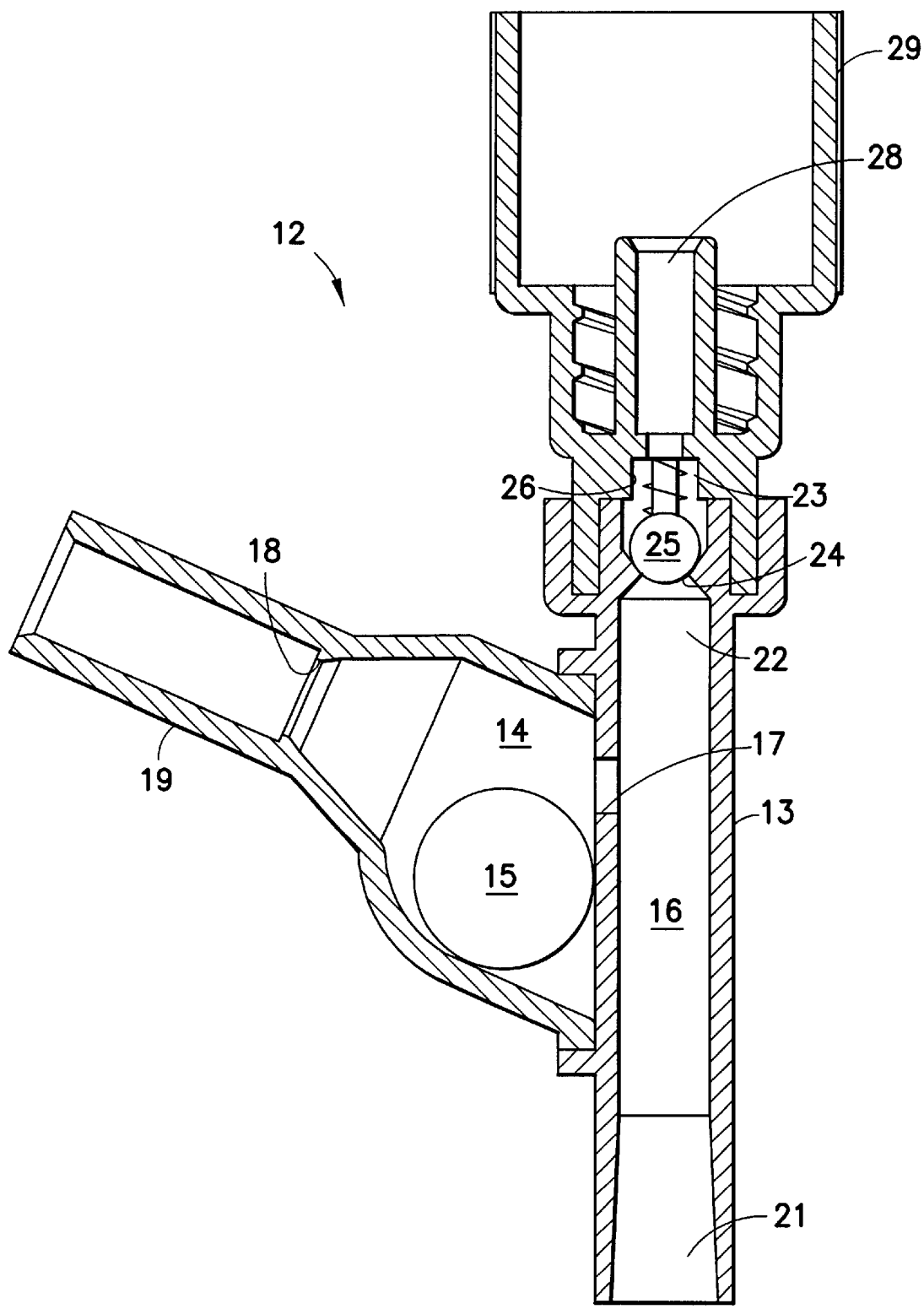
FIG. 2 is a side cross-sectional view of the main body of the filling section of the inventive system in a substantially vertical orientation for pre-delivery loading of the fluid chamber and purging of trapped air therefrom.
Figure 3:
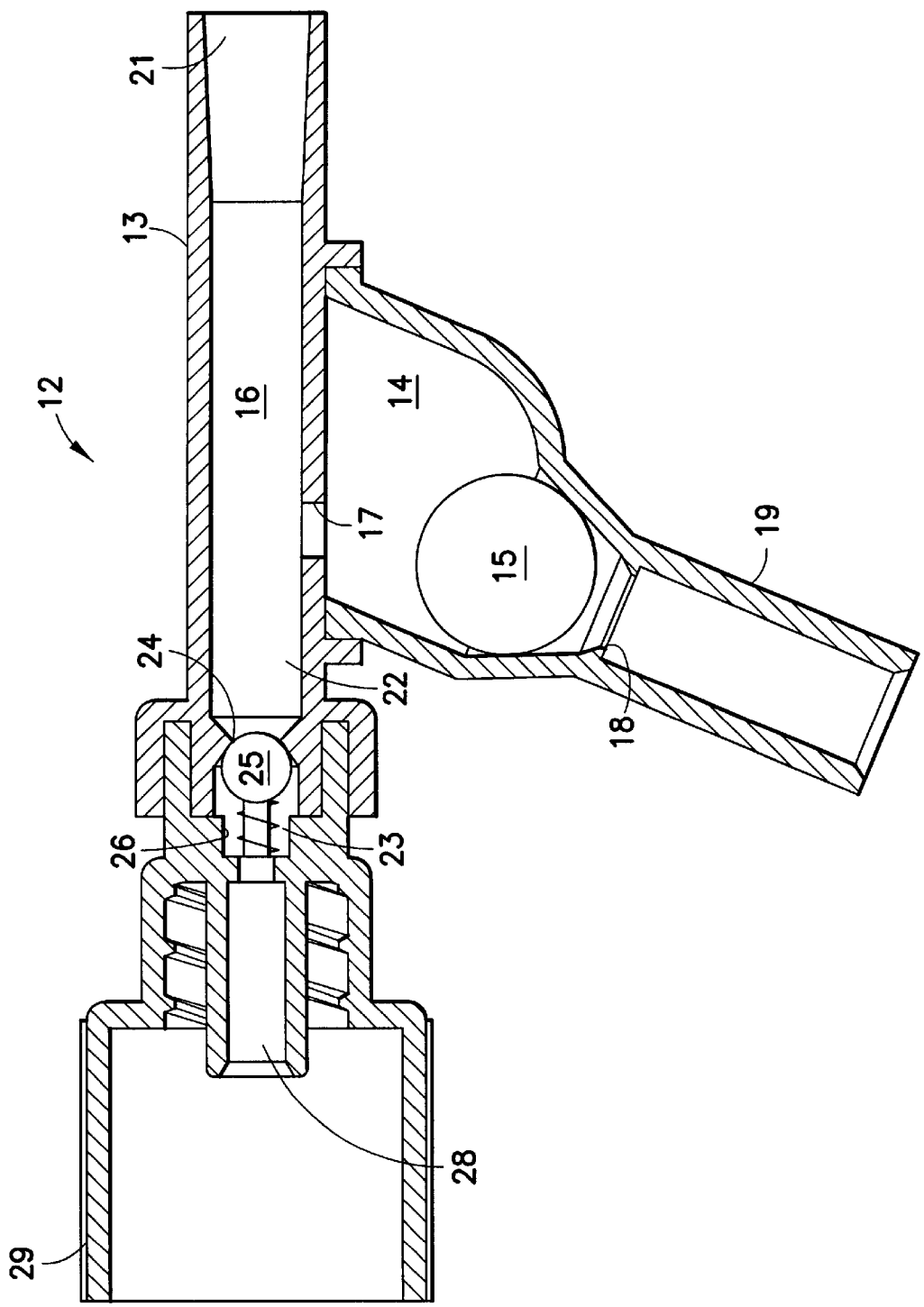
FIG. 3 is a side cross-sectional view of the main body of FIG. 2 in a substantially horizontal orientation for delivery of preloaded fluid from the main body to the patient through the delivery section.

The main body 12 is shown in FIG. 2 in the substantially vertical orientation in which it is predeterminately filled with contrast fluid from the supply container through filling conduit 30. In this orientation the ball 25 is gravitationally displaced from the conically-profiled entrance or seat of inlet opening 18 so that fluid can be freely drawn into the ball chamber 14 and loading chamber 16 by suitable reverse operation of syringe 20. Air initially present within fluid holding chamber 13 can also be expelled, by forward operation of syringe 20, back through the open or unrestricted inlet opening 18 and into the contrast fluid supply container via filling conduit 30 and the vented spike. The check valve closing force that is applied to the ball 25 by spring 23 is selected so as to maintain the check valve in its closed or sealed condition as the air is expelled from holding chamber 13 through the unobstructed valve opening 18. This process of expelling air in holding chamber 13 can be repeated as necessary until chamber 13 is completely evacuated of air and filled with contrast fluid to thereby place the filling section 10 in readiness for delivery of the contained contrast fluid to the patient.

Once all air has been expelled from fluid chamber 13, the main body 12 can be connected to the remainder of the delivery apparatus and reoriented to its contrast fluid delivery position. That position, as seen in FIGS. 1 and 3, places the elongated fluid holding chamber 16 in a substantially horizontal orientation, although it is preferred and generally contemplated that the first end 21 of chamber 16 be disposed slightly or moderately higher than (i.e. elevated with respect to) its opposite second end 22 so that any air or gas that unknowingly or inadvertently remains in chamber 16 will rise toward the first end 21 and, thereby, away from the chamber outlet 24 and outlet tube 28 through which contrast fluid is delivered to the patient. In this substantially horizontal fluid delivery orientation, the valve ball 15 is displaced by the force of gravity onto and into sealing engagement with the seat of inlet opening 18 so that, when the syringe 20 is conventionally operated to deliver contained contrast fluid from main body 12 to the patient, the contained contrast fluid is prevented from unintendedly exiting body 12 through inlet tube 19. Instead, such delivery operation of syringe 20 sufficiently compresses spring 23 to force the contained contrast fluid against the spring-loaded ball 25, which normally closes chamber outlet 24, and thereby open the check valve and permit fluid flow into outlet tube 28 for downstream delivery to delivery section 40 of the inventive system.

As schematically depicted in FIG. 1, the delivery section 40 includes a pair of conventional inline check valves 41 that are connected in series to the outlet tube 28 of the main body 12 of filling section 10, an inline aspirator syringe 48, a first fluid delivery conduit 42 connected between the check valves 41 and an inlet opening 54 of the aspirator syringe, and a second fluid delivery conduit 60 connected at one end to an outlet opening 56 of the aspirator syringe and connected (as through a male luer 62) to or carrying at its other end a conventional catheter or the like through which the contrast fluid is infused or injected into the patient in situ. The first and second conduits 42, 60 may for example take the form of suitable lengths of flexible, plastic, sterile tubing as is well known for use in such infusion applications, as for example coiled tubing for first conduit 42 and uncoiled tubing for second conduit 60. The check valves 41 may be of any appropriate form or design, and although two series-connected check valves are preferred for redundancy, one (or more than two) such check valves may alternatively be employed. It is also contemplated that the filling section 10 may itself carry, permanently or otherwise affixed to its outlet tube 28 as an integral part thereof, either one of the two check valves 41 or an additional such check valve. Similarly, the check valve(s) 41 can alternatively be connected to the main body outlet tube 28 by an additional length (not shown) of sterile tubing, so that the check valve(s) are disposed between the first conduit 42 and such additional length of tubing. It will in any event be appreciated that the function of such check valve(s) 41, without regard to their number or the exact manner of attachment or connection to the main body fluid outlet, is to prevent backflow and contamination of main body 12 by fluid present in second conduit 60 or otherwise downstream of body 12. To further prevent its unintended contamination in the course of connection or disconnection or reattachment of check valves or conduits thereto, main body 12 may additionally be provided with a unitary or otherwise integral protective shroud 29 that surrounds or extends about and beyond the end of outlet tube 28 to avoid contact contamination of the fluid passageway defined by outlet tube 28 as the check valve(s) 41 and/or first delivery conduit 42 or the like are connected thereto or disconnected therefrom.

Figure 4:
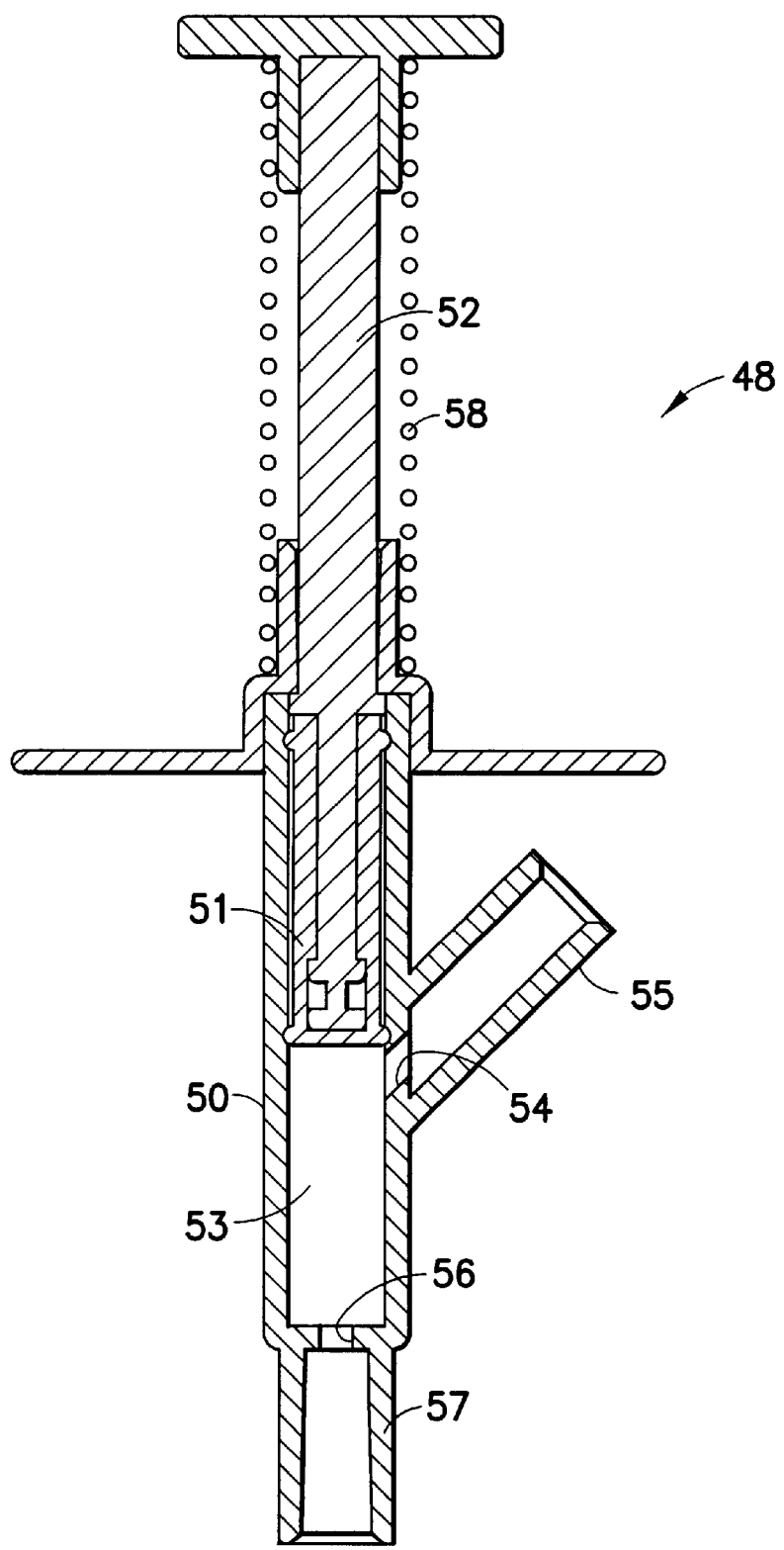
FIG. 4 is a side cross-sectional view of the inline aspiration syringe of the delivery section of the inventive system.

As seen in FIG. 4, the inline aspirator syringe 48 includes a barrel 50 (shown having an optional outwardly-projecting user-graspable tab or member), a manually-operable spring-loaded plunger 51 carried within and normally located at the proximal end of the barrel, the inlet opening 54 (and an associated protective shroud or attachment collar 55) which is defined substantially centrally along and in and through the sidewall of the barrel, the outlet opening 56 (and an associated protective shroud or attachment collar 57) at the other or distal end of the barrel, and a fluid chamber 53 defined within barrel 50 at and proximate its distal end. The plunger 51 is displaceable—from its normal or initial position shown in FIG. 4—by selected manual user depression of the projecting actuator rod 52 against the return urgency of a spring 58 to distally drive the plunger toward the aspirator syringe outlet opening 56. Subsequent automatic or assisted return of plunger 51 to its initial, FIG. 4 position is provided by the return urgency of spring 58, although implementations of the aspiration syringe that omit spring 58 and thereby require manual return of the plunger to its FIG. 4 position are within the intended scope of the invention. The distal end of plunger 51 is located so that inlet opening 54 is unobstructed by plunger 51 in its initial, FIG. 4 position to accommodate the free flow of fluid therethrough and so that, when the plunger is distally displaced from that initial position, its sidewall or the like effectively closes inlet opening 54 to prevent any forced backflow of fluid from fluid chamber 53 (or otherwise from within barrel 50) upstream into first delivery conduit 42. This construction accordingly avoids the necessity of additionally providing, as is common in current contrast fluid delivery systems and the like, separate or other check valves or closure members or devices or the like for preventing backflow through inlet opening 54 as aspirator syringe 48 is operated to, for example, assure or confirm patency of the fluid communication path between the aspiration syringe and the patient. Thus, this advantageous construction of the inline aspiration syringe provides the functionality of heretofore-required valving or the like for effectively closing and then reopening, in an automated manner requiring no user intervention, the aspiration syringe inlet opening 54 as plunger 51 is operatively displaced along barrel 50 from its initial position and henceforth returned thereto.

In use, the fluid delivery system of the invention is first filled with fluid by piercing a storage container of contrast fluid with the vented spike, vertically orienting the main body 12 as shown in FIG. 2 and, through operation of the power syringe 20, drawing in contrast fluid from the storage container and expelling displaced air from the filling section 10 as described hereinabove. The main body is then placed in the substantially horizontal orientation (i.e. preferably with the end 21 of loading chamber 16 at least slightly elevated with respect to the opposite chamber end 22) shown in FIGS. 1 and 3 to allow any remaining air to rise to the first end 21 of loading chamber 16 and to seat the gravity-operated valve ball 15 sealingly against the valve seat inlet opening 18. Power syringe 20 is then operated to drive contrast fluid contained within the chamber 13 of main body 12 against the spring force that normally closes chamber outlet 24, thus displacing ball 25 against the spring urgency to open the one-way fluid delivery check valve, and outwardly from the filling section 10 through main body outlet tube 28. The delivery pressure predeterminately provided by power syringe 20 is further sufficient to force the contrast fluid through and beyond the check valves 41, through the first delivery conduit 42, into the fluid chamber 53 of aspirator syringe 48 through its inlet opening 54, outwardly from chamber 53 through aspirator syringe outlet opening 56, and into and along the second conduit 60 until the entire path along which contrast fluid is to be delivered to the patient has been filled, primed and purged of all air. The catheter can then be emplaced in the patient or, if the catheter is already in place, the distal or downstream end of second conduit 60 can then be connected or attached, as by way of a male luer 62 or the like, to the in situ catheter.

Patency of the contrast fluid delivery conduit 60 to the patient's vein can then be confirmed by manual depression and typically controlled release of the actuator 52 of spring-loaded plunger 51 of the aspirator syringe. Depression of actuator 52 causes plunger 51 to close inlet opening 54 while forcing fluid within fluid chamber 48 and/or second delivery conduit 60 into the patient through the emplaced syringe. With the plunger's subsequent release and return, under or in association with the preferred (but nonetheless optional) urgency of its associated spring 58, to its initial nondisplaced (FIG. 4) position, blood from the patient's vein is drawn back a predetermined distance into second conduit 60, as for example about three inches into conduit 60 if the catheter is properly placed in currently preferred implementations of the inventive system, while inlet opening remains closed by plunger 51. With patency thus confirmed, the loading syringe 20 may then be further operated to inject the desired amount of contrast fluid into the patient at a controlled, predetermined rate and/or pressure.

After the desired volume of contrast fluid has been injected into the patient, the catheter is withdrawn from the vein and the delivery section 40, which includes the at least one check valve 41, can be disconnected or detached from the filling section 10 and discarded. Since the filling section 10 has been completely isolated from any downstream contamination, it may be reused by refilling it with additional contrast fluid from the supply container, which remains connected to the main body 12 by filling conduit 30, and then attaching to the filling section 10 a new, sterile delivery section 40. If desired, one check valve 41 may remain attached or connected to the main body 12 when the remainder of the delivery section 40 (including at least one additional check valve 41) is discarded. It is in any event not necessary to discard the filling section 10, or a connected contrast fluid supply container that contains additional, unused contrast fluid, for one or more patients to whom contrast fluid is to be subsequently delivered, so that the same filling section 10 may accordingly be used repeatedly for multiple imaging procedures with a succession of patients. It is generally contemplated that the filling section 10 will be replaced at least at the end of each day, although other periods of acceptable use may alternatively be employed. It is further within the intended scope of the invention that the filling section may be constructed of materials enabling the filling section, or at least the main body 12 thereof, to be sterilized for multiple or repeated reuse over more extended periods of time.

Thus, while there have shown and described and pointed out fundamental novel features of the invention as applied to preferred embodiments thereof, it will be understood that various omissions and substitutions and changes in the form and details of the methods described and devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. An apparatus for receipt and delivery of fluid for intravenous infusion into a patient in conjunction with an external syringe, said apparatus comprising:

a filling section comprising a main body having a fluid receiving chamber and disposable in a first orientation for predetermined filling of the fluid receiving chamber with fluid from a supply of the fluid located external of said body and in a second orientation for delivery to the patient of fluid contained in the fluid receiving chamber, said main body further comprising a fluid inlet in communication with the receiving chamber, a fluid outlet in communication with the receiving chamber, an opening defined in said body for attachment of the external syringe which is selectively operable for drawing fluid from the fluid supply through said inlet to fill said receiving chamber through said inlet and for ejecting from said main body fluid contained in the receiving chamber through said fluid outlet, a gravity-operated first valve between said fluid inlet and said receiving chamber and located and configured so as to define a closed condition of said first valve that prevents fluid passage through said first valve in said second orientation of said main body and to define an open condition of said first valve that permits fluid passage through said first valve in said first orientation of said main body, and a spring-loaded one-way second valve between said receiving chamber and said fluid outlet; and a delivery section comprising an inline aspiration syringe selectively operable for confirming fluid delivery patency and having a delivery inlet and a delivery outlet, a first fluid conduit connected between said main body fluid outlet and said aspiration syringe delivery inlet, a check valve connected between said first fluid conduit and said main body fluid outlet for preventing return flow of fluid from said first conduit to said main body fluid outlet, and a second fluid conduit connected at one end to said aspiration syringe delivery outlet for intravenously delivering fluid to the patient;

wherein operation of the loading syringe causes fluid contained in said receiving chamber of the main body to be ejected from said main body through said second valve and fluid outlet and to be delivered along said first conduit, into and through said aspiration syringe, and along said second conduit for intravenous infusion into the patient; and wherein said delivery section is disconnectable from said filling section for disposal of the delivery section after use of said delivery section for delivering fluid to the patient without contamination of the filling section so as to permit repeated uses of the filling section for subsequent delivery of fluid to additional patients.

2. An apparatus as in claim 1, wherein said gravity-operated first valve comprises a freely-movable ball disposed in said main chamber and seatable, under gravitational forces in said second orientation of said main body, on a peripheral wall of a valve opening defined between said fluid inlet and said receiving chamber to close said first valve against fluid flow through said valve opening.

3. An apparatus as in claim 2, wherein said main chamber comprises a ball chamber within which said ball is disposed and a loading chamber connected by a fluid transfer opening sized to prevent passage of said ball through said fluid transfer opening.

4. An apparatus as in claim 3, wherein said opening in said main body for accommodating attachment of the external syringe is located in said loading chamber remote from said fluid outlet.

5. An apparatus as in claim 1, wherein said spring-loaded second valve comprises a valve opening, a ball and a coil spring that presses said ball against said valve opening to normally close said second valve.

6. An apparatus as in claim 1, wherein said filling section further comprises a filling conduit for delivering fluid from an external fluid supply container to said receiving chamber and having a first end connected to said main body fluid inlet and a second end adapted for connection to a vented spike for pierced connection to the external fluid supply container.

7. An apparatus as in claim 1, wherein said aspiration syringe further comprises a barrel and a plunger arranged in said barrel for selective movement in a first direction to force fluid into the patient from at least one of said second conduit and said barrel, and in a second direction for drawing at least one of fluid and blood from the patient to confirm patency.

8. An apparatus as in claim 7, wherein said aspiration syringe further comprises a spring associated with said plunger for applying a return urgency to said plunger to assist movement of the plunger in said second direction.

9. An apparatus as in claim 7, wherein said delivery inlet of the aspiration syringe is defined in said barrel, and wherein said plunger is located in said barrel and configured so that the plunger is normally disposed in an initial position noninterferringly remote from said delivery inlet and, as the plunger is selectively moved in said first direction from said initial position and in said second direction to return to said initial position the plunger closes said delivery inlet to prevent backflow of fluid from said aspiration syringe into said first fluid conduit during said selective movement of the plunger.

10. An apparatus as in claim 1, wherein at least one of said first conduit and said second conduit comprises a length of flexible tubing.

11. In an apparatus for receipt and delivery of fluid for intravenous infusion into a patient in conjunction with an external syringe, a first fluid delivery conduit and a second fluid delivery conduit, the improvement comprising:

a filling section comprising a main body having a fluid receiving chamber and disposable in a first orientation for predetermined filling of the fluid receiving chamber with fluid from a supply of the fluid located external of said body and in a second orientation for delivery to the patient of fluid contained in the filled receiving chamber, said main body further comprising a fluid inlet in communication with the receiving chamber, a fluid outlet in communication with the receiving chamber, an opening defined in said body for attachment of the external syringe which is selectively operable for drawing fluid from the fluid supply through said inlet to fill said receiving chamber through said inlet and for ejecting from said main body fluid contained in the receiving chamber through said fluid outlet, a gravity-operated first valve between said fluid inlet and said receiving chamber and located and configured so as to define a closed condition of said first valve that prevents fluid passage through said first valve in said second orientation of said main body and to define an open condition of said first valve that permits fluid passage through said first valve in said first orientation of said main body, and a spring-loaded one-way second valve between said receiving chamber and said fluid outlet, and a delivery section comprising an aspiration syringe selectively operable for confirming fluid delivery patency and having a delivery inlet connectable to the main body fluid outlet by the first fluid delivery conduit and a delivery outlet connectable to the patient by the second fluid delivery conduit, wherein operation of the loading syringe causes fluid contained in said receiving chamber of the main body to be ejected from said main body through said second valve and fluid outlet and to be delivered along the first delivery conduit, into and through said aspiration syringe, and along the second delivery conduit for intravenous infusion into the patient; and wherein said delivery section is disconnectable from said filling section for disposal of the delivery section after use of said delivery section for delivering fluid to the patient without contamination of the filling section so as to permit repeated uses of the filling section for subsequent delivery of fluid to additional patients.

12. In an apparatus in accordance with claim 11, wherein said gravity-operated first valve comprises a freely-movable ball disposed in said main chamber and seatable, under gravitational forces in said second orientation of said main body, on a peripheral wall of a valve opening defined between said fluid inlet and said receiving chamber to close said first valve against fluid flow through said valve opening.

13. In an apparatus in accordance with claim 12, wherein said main chamber comprises a ball chamber within which said ball is disposed and a loading chamber connected by a fluid transfer opening sized to prevent passage of said ball through said fluid transfer opening.

14. An apparatus as in claim 13, wherein said opening in said main body for accommodating attachment of the external syringe is located in said loading chamber remote from said fluid outlet.

15. In an apparatus as in claim 11, wherein said spring-loaded second valve comprises a valve opening, a ball and a coil spring that presses said ball against said valve opening to normally close said second valve.

16. In an apparatus as in claim 11, wherein said aspiration syringe further comprises a barrel and a plunger arranged in said barrel for selective movement in a first direction to force fluid into the patient from at least one of said second conduit and said barrel, and in a second direction for drawing at least one of fluid and blood from the patient to confirm patency.

17. In an apparatus as in claim 16, wherein said aspiration syringe further comprises a spring associated with said plunger for applying a return urgency to said plunger to assist movement of the plunger in said second direction.

18. In an apparatus as in claim 16, wherein said delivery inlet of the aspiration syringe is defined in said barrel, and wherein said plunger is located in said barrel and configured so that the plunger is normally disposed in an initial position noninterferringly remote from said delivery inlet and, as the plunger is selectively moved in said first direction from said initial position and in said second direction to return to said initial position the plunger closes said delivery inlet to prevent backflow of fluid from said aspiration syringe into the first fluid delivery conduit during said selective movement of the plunger.

* * * * *